(12) United States Patent
Pugh et al.

(10) Patent No.: US 8,808,257 B2
(45) Date of Patent: Aug. 19, 2014

(54) METHODS AND APPARATUS FOR PULSATILE RELEASE OF MEDICAMENTS FROM A PUNCTAL PLUG

(75) Inventors: Randall B. Pugh, Jacksonville, FL (US); Jason M. Tokarski, Jacksonville, FL (US); Bret A. Coldren, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 12/857,885

(22) Filed: Aug. 17, 2010

(65) Prior Publication Data

US 2011/0054418 A1 Mar. 3, 2011

Related U.S. Application Data

(60) Provisional application No. 61/238,470, filed on Aug. 31, 2009.

(51) Int. Cl.
| | | |
|---|---|---|
| A61M 35/00 | (2006.01) | |
| A61K 9/00 | (2006.01) | |
| A61F 9/007 | (2006.01) | |
| A61K 9/50 | (2006.01) | |
| A61F 9/00 | (2006.01) | |
| A61M 31/00 | (2006.01) | |

(52) U.S. Cl.
CPC ............. *A61F 9/0026* (2013.01); *A61K 9/0051* (2013.01); *A61K 9/0019* (2013.01); *A61F 9/00772* (2013.01); *A61K 9/0021* (2013.01); *A61K 9/5031* (2013.01); *A61M 31/00* (2013.01)
USPC ........................................ 604/294

(58) Field of Classification Search
CPC .............. A61F 9/00772; A61F 9/0017; A61F 2210/0004; A61K 9/0051
USPC ........................... 424/427, 428; 604/294, 298
See application file for complete search history.

(56) References Cited

U.S. PATENT DOCUMENTS

| | | | |
|---|---|---|---|
| 5,017,381 A | 5/1991 | Maruyama et al. | |
| 5,472,708 A | 12/1995 | Chen | |
| 6,287,295 B1 | 9/2001 | Chen | |
| 2005/0129731 A1* | 6/2005 | Horres et al. | 424/423 |

(Continued)

FOREIGN PATENT DOCUMENTS

| | | |
|---|---|---|
| CA | 2031864 | 11/1991 |
| WO | WO 0062760 A1 | 10/2000 |

(Continued)

OTHER PUBLICATIONS

PCT International Search Report, dated Oct. 15, 2010, for PCT Int'l Appln. No. PCT/US2010/046442.

(Continued)

*Primary Examiner* — Aarti B Berdichevsky
*Assistant Examiner* — Bradley Osinski

(57) ABSTRACT

This invention discloses methods and apparatus for providing pulsatile release of active agents via a punctal plug inserted into a punctum. A tube is provided which may be inserted into a cavity of a punctal plug. One or more pulsatile delivery units are arranged in a generally linear fashion within the tube. The pulsatile delivery units include a core comprising the active agent and an encapsulation layer around the core.

18 Claims, 5 Drawing Sheets

(56) References Cited

U.S. PATENT DOCUMENTS

| | | | |
|---|---|---|---|
| 2007/0269487 A1* | 11/2007 | de Juan et al. | 424/427 |
| 2007/0298075 A1* | 12/2007 | Borgia et al. | 424/428 |
| 2008/0038317 A1* | 2/2008 | Chang et al. | 424/428 |
| 2008/0177153 A1 | 7/2008 | Bachman | |

FOREIGN PATENT DOCUMENTS

| | | |
|---|---|---|
| WO | WO 2006014793 A1 | 2/2006 |
| WO | WO 2006031658 A2 | 3/2006 |
| WO | WO 2007115259 A2 | 10/2007 |
| WO | WO 2007/149832 A2 | 12/2007 |
| WO | WO 2007149771 A2 | 12/2007 |
| WO | WO 2009/035562 A2 | 3/2009 |
| WO | WO 2009/097468 A2 | 8/2009 |
| WO | WO 2009137673 A1 | 11/2009 |

OTHER PUBLICATIONS

Russian Office Action for corresponding Application No. 2012112548/14.

Notification of Reasons for Refusal from the Japanese Patent Office mailed Feb. 4, 2014.

\* cited by examiner

METHODS AND APPARATUS FOR PULSATILE RELEASE OF MEDICAMENTS FROM A PUNCTAL PLUG

RELATED APPLICATIONS

This application claims priority to Provisional Patent Application U.S. Ser. No. 61/238,470 which was filed on Aug. 31, 2009, the contents of which are relied upon and incorporated by reference.

FIELD OF USE

This invention describes methods and apparatus for dispensing one or more materials, such as a medicament, from a punctal plug reservoir and, in some embodiments, dispensing a drug component in a form conducive to pulsatile release into a cavity of a punctal plug.

BACKGROUND

Medicaments frequently are administered to the eye for the treatment of ocular diseases and disorders. Conventional means for delivering medicaments to the eye involve topical application to the surface of the eye. The eye is uniquely suited to topical administration because, when properly constituted, topically applied medicaments can penetrate through the cornea and rise to therapeutic concentration levels inside the eye. Medicaments for ocular diseases and disorders may be administered orally or by injection, but such administration routes are disadvantageous in that, in oral administration, the active agent may reach the eye in too low a concentration to have the desired pharmacological effect and their use is complicated by significant, systemic side effects and injections pose the risk of infection.

The majority of ocular medicaments are currently delivered topically using eye drops which, though effective for some applications, are inefficient. When a drop of liquid is added to the eye, it overfills the conjunctival sac, the pocket between the eye and the lids, causing a substantial portion of the drop to be lost due to overflow of the lid margin onto the cheek. In addition, a substantial portion of the drop that remains on the ocular surface is drained into the lacrimal puncta, diluting the concentration of the drug.

Other methods allow for the eluding of a medicament over a period of time. However, some medicaments are most efficacious when periodically delivered in a predetermined dosed amount. Accordingly, alternative methods and devices for delivering medicaments to an ophthalmic area may be beneficial.

SUMMARY

The present invention relates to devices for pulsatile administration of a medicament via a punctal plug, and includes methods and apparatus for placing a medicament in a punctal plug cavity wherein the medicament can subsequently be delivered to a patient on a pulsatile basis with the punctal plug inserted into a punctum.

According to the present invention, a tube is provided which may be inserted into a cavity of a punctal plug. One or more pulsatile delivery units are arranged in a generally linear fashion within the tube. The pulsatile delivery units include a core comprising the active agent and an encapsulation layer around the core.

In some embodiments, a boundary layer is included between a first pulsatile delivery unit and a second pulsatile delivery unit. Additional embodiments include a boundary layer between a pulsatile delivery unit and an opening in the cavity of the punctal plug. By way of non-limiting example, a boundary layer may include one or more of: a biodegradable membrane; a semi-porous membrane or a mesh.

In another aspect, in some embodiments, an active agent-containing material may include a poly(epsilon-caprolactone) and ethylene vinyl acetate. The poly(epsilon-caprolactone) and ethylene vinyl acetate may each be present, for example, in an amount of about 50 weight percent.

In another aspect, in some embodiments, a first pulsatile delivery unit may include a first active-agent containing material comprising a relatively low concentration of the active agent and a second pulsatile delivery unit may include a second active-agent containing material comprising a relatively high concentration.

Other embodiments are included within the scope of the following specification and claims and accompanying drawings.

DETAILED DESCRIPTION OF THE INVENTION

Figure 1A:
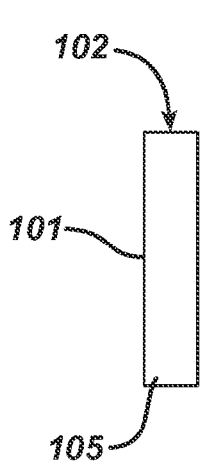
FIG. 1 illustrates a punctal plug and method for deposition of pulse doses into a punctal plug according to some embodiments of the present invention.
Figure 1B:
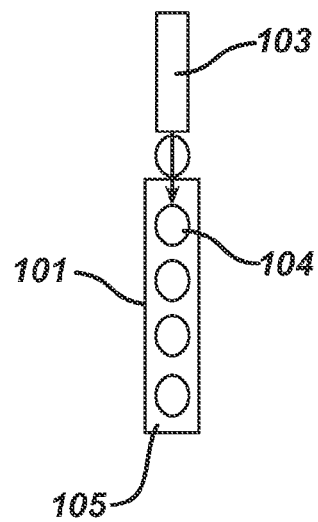
Figure 1C:
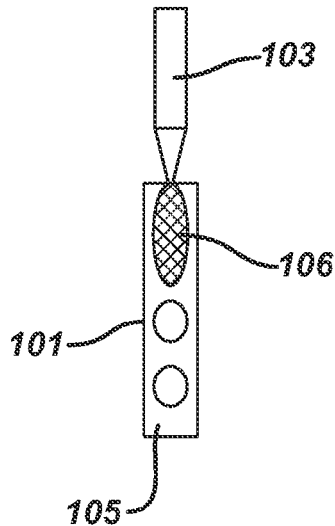
Figure 1D:
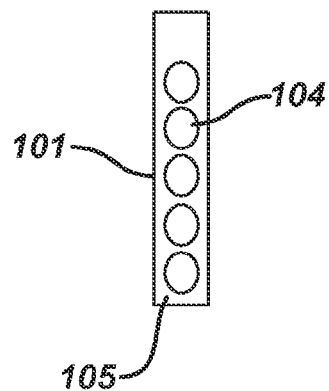
Figure 1E:
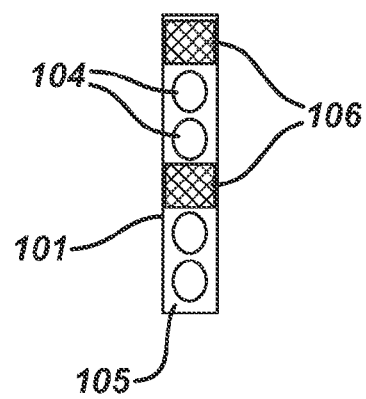

The present invention includes apparatus and methods for forming punctal plugs that may be used to deliver active agents to one or both of the nasolacrimal ducts and to the tear fluid of the eye, wherein the delivery of the active agent takes place in a pulsatile pattern. A location for dissemination of an active agent is positioned to release the active agent into tear fluid and preferably with minimal release into the nasolacrimal duct. The pulsatile pattern is accomplished by linearly aligning water soluble encapsulated beads or other pulsatile delivery unit in a carrier, such as a tube and regulating exposure of each pulsatile delivery unit to an aqueous solution, such as tear fluid. As a first pulsatile delivery unit is exposed to the aqueous solution and dissolved, a medicament encapsulated within the pulsatile delivery unit is then released into the nasolacrimal duct. Dissolving of a first pulsatile delivery unit and consequent release of a first dose of medicament then exposes a second pulsatile delivery unit to the aqueous solution. The pattern repeats itself as the linearly aligned pulsatile delivery units are dissolved and expose a next unit to the aqueous solution.

Some embodiments include apparatus and methods for forming a punctal plug comprising, consisting essentially of, and consisting of: a punctal plug body having a first end and a second end; a surface extending between the two ends; a reservoir contained within the punctal plug body wherein the reservoir comprises, consists essentially of and consists of an active agent-containing material and an active agent, wherein the active agent is linearly present in a pulsatile dosing bead. The punctal plug may additionally comprise a defined area, such as an opening in the punctal plug, which is more conducive to elution or other dissemination of the active agent from the punctal plug cavity to an area proximate to the punctal plug. Some preferred embodiments include an area conducive to dissemination of the active agent comprising an opening with a diameter which is smaller than a diameter of the cavity containing the active ingredient.

The present invention additionally provides devices, and methods for their use and manufacture, that can be used to deliver active agents into a cavity in a punctal plug in a controlled manner.

It has been known to fill a cavity in a punctal plug via insertion of a rod, or other rigid or semi rigid article. The rod can include a pharmaceutical or other medicament. However, previously known administration relied upon an active agent eluding from the plug. According to the present invention, a linear progression of pulses of an active agent is delivered.

DEFINITIONS

As used herein, the term "active agent" refers to an agent capable of treating, inhibiting, or preventing a disorder or a disease. Exemplary active agents include, without limitation, pharmaceuticals and nutraceuticals. Preferred active agents are capable of treating, inhibiting, or preventing a disorder or a disease of one or more of the eye, nose and throat.

As used herein, the term "punctal plug" refers to a device of a size and shape suitable for insertion into the inferior or superior lacrimal canaliculus of the eye through, respectively, the inferior or superior lacrimal punctum.

As used herein, the term "opening" refers to an opening in the punctal plug body of a device of the invention of a size and shape through which the active agent can pass. Preferably, only the active agent can pass through the opening. The opening may be covered with a membrane, mesh, grid 106 or it may be uncovered. The membrane, mesh, or grid may be one or more of porous, semi-porous, permeable, semi-permeable, and biodegradable.

Referring now to FIG. 1, at 1A a medicament tube 101 is illustrated with an opening 102 which fluidly communicates with a cavity 105 formed in the medicament tube 101 body. At 1B, a dispenser tip 103 is positioned proximate to the opening 102 and dispenses a pulsatile delivery unit 104 through the opening 102 and into the cavity 105. Examples of active agents that can be included in the pulsatile delivery unit 104 include one or more of: bimatoprost; bimatoprost with an ethyleneoxynalacetate. At 1C, in some embodiments, the cavity 105 may also be filled by the dispenser tip 103 with a boundary layer 106 or membrane. Preferred embodiments include a boundary layer 106 that is soluble in tear fluid. A thickness of a boundary layer 106 and a time to dissolve a boundary layer when it is exposed to an aqueous solution can be correlated in order to design in a predetermined amount of time for an aqueous solution, such as tear fluid to access linearly aligned pulsatile delivery units. Accordingly, the boundary layer thickness and physical characteristics can be adjusted to control a time period between pulses of medicaments being delivered to an eye, or nasolacrimal duct.

At 1D, in some embodiments the tube 105 can contain multiple pulsatile delivery units 104 comprising a sphere of encapsulated aqueous solution or oil. Other embodiments include an encapsulated compound including an active agent and an excipient. Each pulsatile delivery unit may include doses of an active agent or medicament, of between, by way of non-limiting example, 10 (ten) picoliters and 100,000 (ten thousand) picoliters. The pulsatile delivery unit 104 may also include one or more excipients.

The cavity may be any size and/or shape that a punctal plug design may support. In some embodiments, the volume of the cavity 105 will be about between 10 and 100 nanoliters. Some specific embodiments include a cavity volume of about between 40 nanoliters and 50 nanoliters. An opening 102 to a cavity into which a dispenser tip may be inserted, may be, for example, include a diameter of between about 0.1 mm to 0.4 mm and a cavity 105 may include a depth of between about 0.5 mm to about 2.0 mm. In some preferred embodiments, the opening 102 will be about 0.2 mm and the depth of the cavity will be about 1.5 mm. Additional preferred aspects of embodiments can include a design with a 0.385 diameter and 1.5 mm length with a cavity volume of 175 nL.

The active agent may be dispersed throughout the active agent-containing pulsatile delivery unit 104 or dissolved within the pulsatile delivery unit 104. Alternatively, the active agent may be contained in inclusions, particulates, droplets, or micro-encapsulated within the pulsatile delivery unit 104. Still as another alternative, the active agent may be covalently bonded to the pulsatile delivery unit 104 and released by hydrolysis, enzymatic degradation and the like. Yet as another alternative, the active agent may be in a reservoir within the pulsatile delivery unit 104.

At 1F pulsatile delivery units 104 may be separated by one or more membrane layers 106. The membrane layers 106 may include various properties. Embodiments can therefore include membrane layers comprising one or more of: biodegradable semi-permeable membranes, non-biodegradable semi-permeable membranes, pores and combinations thereof.

Figure 2:
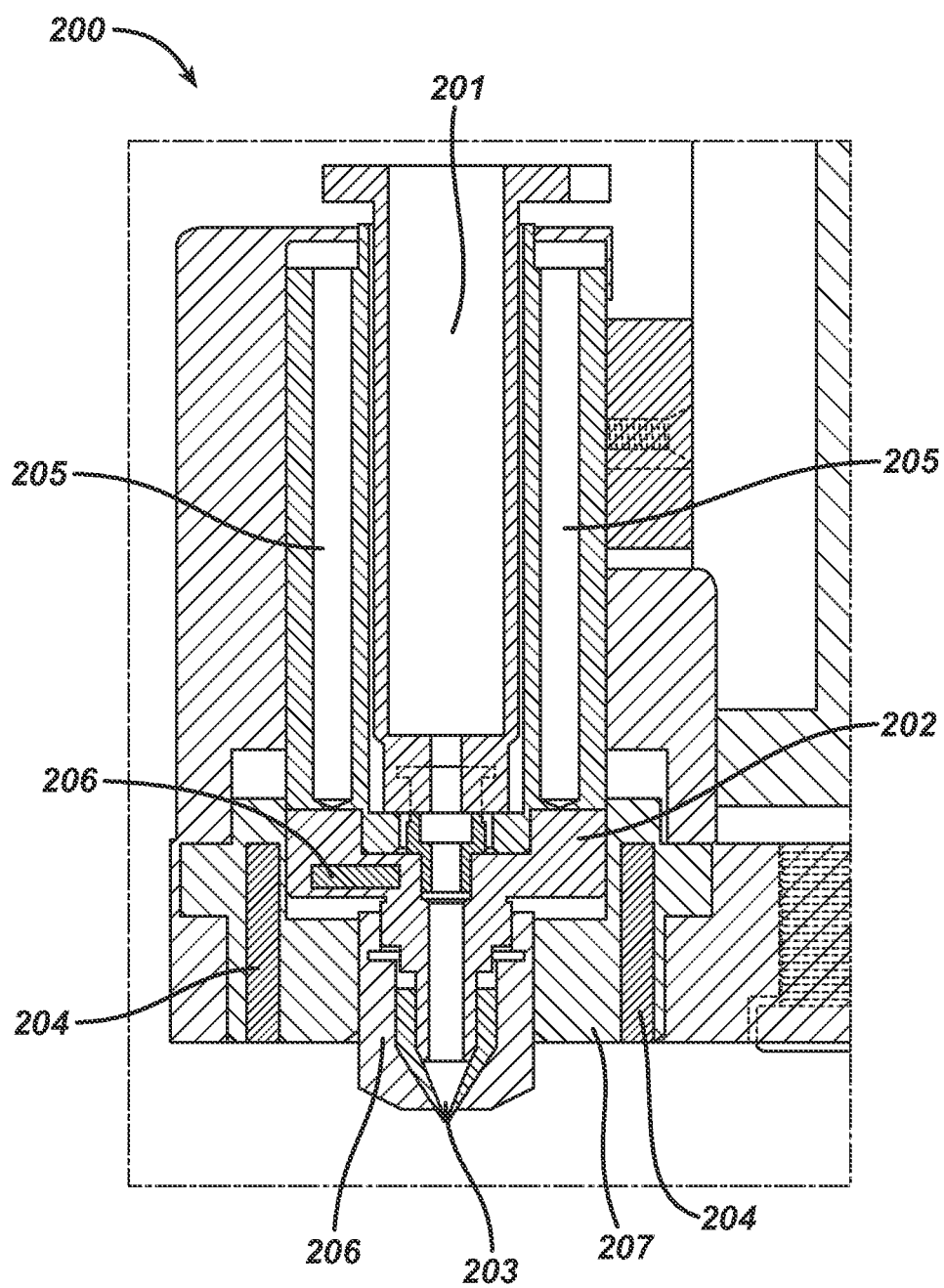
FIG. 2 illustrates apparatus for punctal plug deposition according to some embodiments of the present invention.

Referring now to FIG. 2, an example of some embodiments of the present invention which include a punctal plug active agent pump 200 for depositing the pulsatile delivery unit 104 into a cavity 105 of a medicament tube 101 (illustrated in FIG. 1). Generally, the pump 200 includes a reservoir for containing pulsatile delivery units 104, such as a cartridge 201, mounted in a pump body 207 and attached to provide fluid communication to a dispenser tip 203. The cartridge 201 can include, for example, a modified removable syringe with a large dispensing opening.

The cartridge 201 can be formed from a polycarbonate, stainless steel or other rigid or semi-rigid material. In some preferred embodiments, the cartridge is formed from a material that can be sterilized and also withstand heating during the deposition process. Additionally, in some embodiments, the cartridge 201 will have an end proximate to the dispenser tip 203 and an end distal to the dispenser tip, wherein the end proximate to the dispenser tip can include a lure lock mechanism for securing the cartridge 201 to a dispenser body 202. Other locking or fastening mechanisms may also be used to secure the cartridge 201 in a position proximate to and in fluid communication with the dispenser tip 203. Some embodiments may therefore include designs of a polycarbonate or stainless steel syringe.

Some embodiments can include a positive pressure pump with a computer controlled valve, which control starts and stops dispensing of pulsatile delivery units 104. A computer controlled valve provides active valving to control flow characteristics. In some embodiments, the present invention may dispense very small volumes of an active agent-containing in a pulsatile delivery unit 104. Some embodiments can include volumes of 50 picoliters or less and in some preferred embodiments, volumes of between 20 picoliters to 60 picoliters.

Some preferred embodiments will include one or more temperature control devices 204-206 for cooling or heating the pulsatile delivery unit 104 while it is in one or more of: a) the cartridge 201; b) the dispenser body 202; and c) the dispenser tip 203. The temperature control devices 204-206 can include, for example, one or more of: a thermoelectric device, electrically resistive elements and temperature controlled fluid paths. As illustrated, in some embodiments, a temperature control device 205 may be located along side the cartridge 201 and allow the material with an active ingredient 104 to be kept at an elevated temperature while in the cartridge 201. Some embodiments can also include a temperature control device 204 in or proximate to the pump body 207. Some embodiments may also include temperature requirements that may be adjusted according to material properties excipients to be deposited.

In another aspect, some embodiments of the present invention include a temperature probe 206. The temperature probe can include a transducer for providing a digital or analog output indicating a temperature of a designated portion of the punctal plug active agent pump 200. Embodiments can include an electronic feedback circuit (not shown), which allows control of an amount of heat applied to the active ingredient 104. In some embodiments, the feedback constitutes a closed loop feedback design.

Additionally, in some embodiments, an amount of heat applied to the pulsatile delivery unit 104 can be used to control a formability factor of a material containing an active ingredient 104. Typically, a higher amount of heat applied will lower the rigidity of the pulsatile delivery unit 104 and allow for less pressure to be applied to move the pulsatile delivery unit 104 through the punctal plug active agent pump 200. By way of example, a pulsatile delivery unit 104 can be dispensed through the dispenser tip 203 at a temperature of between 40° C. and 80° C. and in some preferred embodiments at a temperature of between 60° C. and 70° C. In some particular embodiments, a punctal plug 101 into which the material containing the active pulsatile delivery unit 104 is dispensed is also heated to a temperature of between 40° C. and 80° C. In some embodiments, the application of heat to the punctal plug 101 can provide additionally elasticity to the plug during the deposition allowing the cavity 105 to expand and more easily accept the material containing an active ingredient 104. In various embodiments, a preferred temperature may be based upon one or more of: an active ingredient used; an excipient included in the material containing an active ingredient 104; and a material used to encapsulate a pulsatile delivery unit 104.

Figure 3:
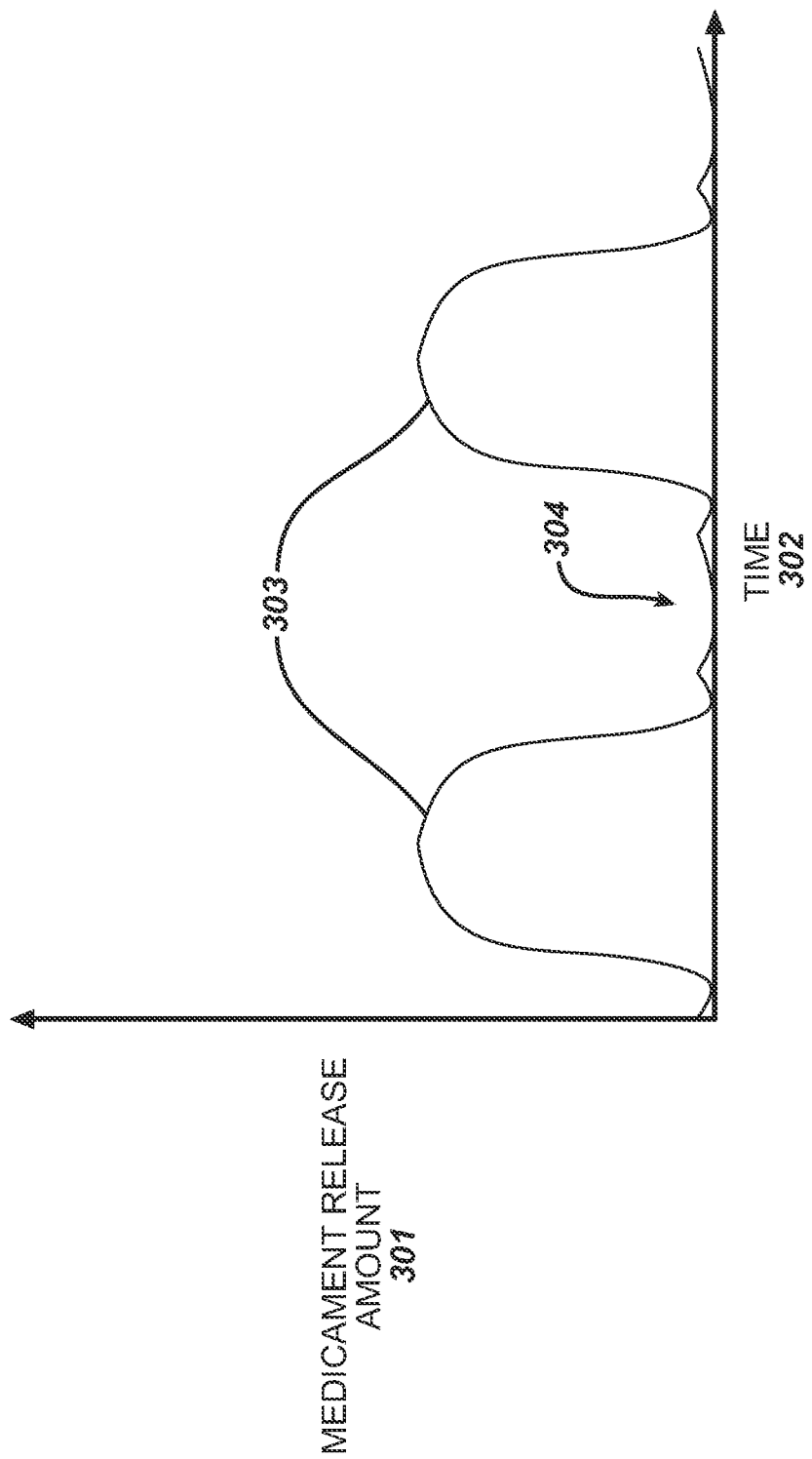
FIG. 3 illustrates a block graph of an amount of medicament delivered via pulsatile delivery over a period of time.

Referring now to FIG. 3, a graph illustrates a generalized release pattern in pulsatile release. Over time 302, pulses in medicament release 303 are experienced. A time period of lower medicament release or essentially no medicament release 302 are experienced in between the pulses 302.

In some embodiments, a boundary layer 106 can be included within a medicament tube 101 in order to create a time period of lower medicament release or essentially no medicament release 302.

According to some embodiments of the present invention the active agent is released from the medicament tube 101 in a consistent pulsatile pattern, meaning in generally equal volume pulses and of generally equal concentration over a period of time by using an active agent-containing pulsatile delivery unit 104 in which the agent is present in a similar size pulse (as dependent upon a similar size pulsatile delivery unit). The pulses 303 may also be of similar concentration in each of the pulsatile delivery unit 104. Additional embodiments include a device that exhibits a "burst" or immediate release upon insertion of an amount of active agent that is greater than the average release of other pulsatile delivery units 104. Still other embodiments include varying one or more of: the size of a pulsatile delivery unit 104; a concentration of medicament within the pulsatile delivery unit 104, the spacing of the pulsatile delivery units 104.

Some exemplary embodiments can also include pulsatile delivery unit 102 containing a material with a mix of excipients and active agents. Pre-mixing apparatus and processes may include twin-screw compounding, chaotic mixing, solvent mixing, or spray drying, or other mixing mechanisms. An exemplary compound can include: 25% bimatoprost as an active agent; 37.5% ethylene vinyl acetate, EVA as a first excipient and 37.5% polycaprolactone, PCL as a second excipient.

The pre-mixed material can be loaded into the heated or non-heated syringe 200 as pellets. Pellets are not a requirement; the active agent can be in the form of one or more of: a powder, fluff and other mediums. Additionally, in some embodiments, such as those in which it is desired to avoid multiple thermal cycle exposure of an active agent and/or to minimize air bubbles, the heated syringe may be directly attached to the micro-compounder so that the pre-mixed material is directly supplied into a nano-dosing dispensing system, such as those described above, without having to cool it to room temperature or lower. As such, in some embodiments the material containing an active agent may be supplied to the nano-dispensing system in a melt form.

In another aspect of the present invention, a gradient of concentration of active agent released may be controlled by placing pulsatile delivery units 102 with more active agent at one location in a linear progression and a material containing an active agent 104 in another concentration at another relative linear position. Alternatively, the matrix may be have a gradient, meaning that one section of the pulsatile delivery unit 104 has a first concentration and the concentration abruptly changes to a second, different concentration in an adjacent section of the matrix. The diffusivity for the active agent may also be spatially controlled by varying one or more of the chemical composition, porosity, and crystallinity of the active agent-containing pulsatile delivery unit 104.

Figure 4:
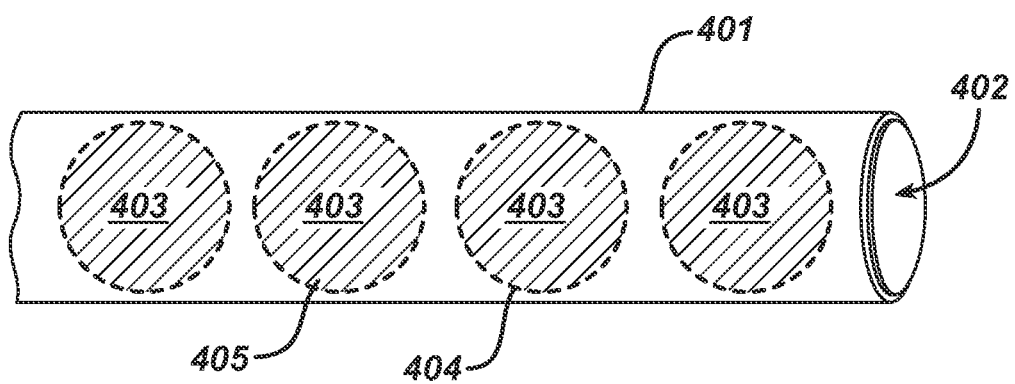
FIG. 4 illustrates a pulsatile medicament delivery package.

Referring now to FIG. 4, a medicament tube 401 is illustrated with multiple pulsatile delivery units 403 arranged in a generally linear fashion. A boundary material 402 is also viewable in a cutaway of the medicament tube 401. The linear arrangement enables on pulsatile delivery unit at a time to be accessed by body fluids and dispersed into the eye or nasolacrimal duct.

As illustrated, the pulsatile delivery units 403 include an encapsulation layer 404 and a medicament core 405. Encapsulation may be accomplished via any known method including, for example Precision Particle Fabrication (PPF) technology for the production of monodisperse liquid-filled microcapsules containing an oil or aqueous core or double-walled microspheres. Examples of encapsulated pulsatile delivery units can include, monodisperse polymeric microcapsules encapsulating an oil or aqueous core in or double-walled (polymer core/polymer shell) microcapsules. Molecules can be localized to the core or shell phase to enable advanced controlled release profiles, including the pulsatile active agent delivery.

Figures 5A, 5B, 5C:
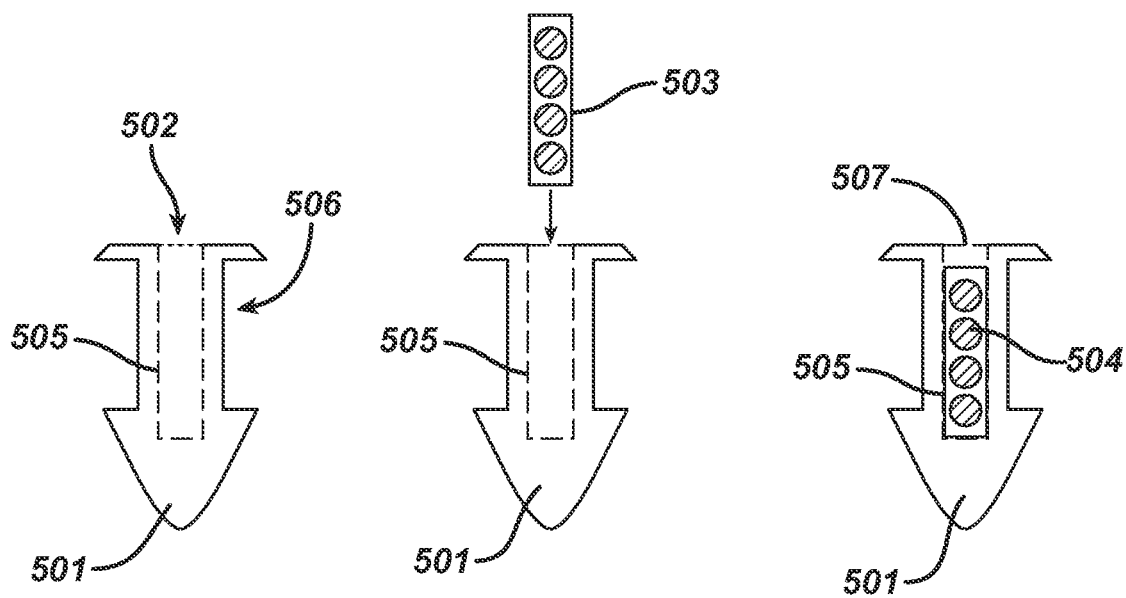
FIGS. 5A-5C illustrate a punctal plug with a pulsatile release insert.

Referring now to FIG. 5, at 5A, punctal plug devices 501 formed according to the present invention may contain a reservoir or cavity 505 within the punctal plug body 506, with an opening 502 accessing the cavity 505. At 5B, one or more medicament tube 503 containing one or more pulsatile release units 504 is inserted into the cavity 505. The pulsatile release units preferably contain at least one active agent. At 5C the medicament tube is fully inserted into the punctal plug and in some embodiments includes a seal 507 that remains intact until utilized the punctal plug device 501 in placed a patient.

The active agent-containing material useful in the devices of the invention is any material that is capable of containing the active agent, does not alter the chemical characteristics of the active agent, and does not significantly chemically degrade or physically dissolve when placed in contact with ocular fluids. Preferably, the active agent-containing material is non-biodegradable, meaning that it does not degrade to a substantial degree upon exposure to biologically active substances typically present in mammals. Additionally, the active agent-containing material is capable of releasing the active agent by one or more of diffusion, degradation, or hydrolyzation. Preferably, the active agent-containing material is a polymeric material, meaning that it is a material made of one or more types of polymers.

When the active agent-containing material is combined with the active agent, the material may also contain one or more materials that are insoluble in water and non-biodegradable, but from which the active agent can diffuse. For example, if the active agent-containing material is a polymeric material, the material may be composed of one or more polymers that are insoluble in water and non-biodegradable.

Suitable polymeric materials for the active agent-containing material include, without limitation, hydrophobic and hydrophilic absorbable and non-absorbable polymers. Suitable hydrophobic, non-absorbable polymers include, without limitation, ethylene vinyl alcohol ("EVA"), fluorinated polymers including without limitation, polytetrafluoroethylene ("PTFE") and polyvinylidene fluoride ("PVDF"), polypropylene, polyethylene, polyisobutylene, nylon, polyurethanes, polyacrylates and methacrylates, polyvinyl palmitate, polyvinyl stearates, polyvinyl myristate, cyanoacrylates, epoxies, silicones, copolymers thereof with hydrophobic or hydrophilic monomers, and blends thereof with hydrophilic or hydrophobic polymers and excipients.

Hydrophilic, non-absorbable polymers useful in the invention include, without limitation, cross-linked poly(ethylene glycol), poly(ethylene oxide), poly(propylene glycol), poly(vinyl alcohol), poly(hydroxyethyl acrylate or methacrylate), poly(vinylpyrrolidone), polyacrylic acid, poly(ethyloxazoline), and poly(dimethyl acrylamide), copolymers thereof with hydrophobic or hydrophilic monomers, and blends thereof with hydrophilic or hydrophobic polymers and excipients.

Hydrophobic, absorbable polymers that may be used include, without limitation, aliphatic polyesters, polyesters derived from fatty acids, poly(amino acids), poly(ether-esters), poly(ester amides), polyalkylene oxalates, polyamides, poly(iminocarbonates), polycarbonates, polyorthoesteres, polyoxaesters, polyamidoesters, polyoxaesters containing amine groups, phosphoesters, poly)anhydrides), polypropylene fumarates, polyphosphazenes, and blends thereof. Examples of useful hydrophilic, absorbable polymers include, without limitation, polysaccharides and carbohydrates including, without limitation, crosslinked alginate, hyaluronic acid, dextran, pectin, hydroxyethyl cellulose, hydroxy propyl cellulose, gellan gum, guar gum, keratin sulfate, chondroitin sulfate, dermatan sulfate, proteins including, without limitation, collagen, gelatin, fibrin, albumin and ovalbumin, and phospholipids including, without limitation, phosphoryl choline derivatives and polysulfobetains.

More preferably, the active agent-containing material is a polymeric material that is polycaprolactone. Still more preferably, the material is poly(epsilon-caprolactone), and ethylene vinyl acetate of molecular weights between about 10,000 and 80,0000. About 0 to about 100 weight percent polycaprolactone and about 100 to about 0 weight percent of the ethylene vinyl acetate are used based on the total weight of the polymeric material and, preferably, about 50% each of polycaprolactone and ethylene vinyl acetate is used.

The polymeric material used is preferably greater than about 99% pure and the active agents are preferably greater than about 97% pure. One of ordinary skill in the art will recognize that in compounding, the conditions under which compounding is carried out will need to take into account the characteristics of the active agent to ensure that the active agents do not become degraded by the process. The polycaprolactone and ethylene vinyl acetate preferably are combined with the desired active agent or agents, micro-compounded, and then extruded.

In a preferred embodiment, the active agent-containing material is a polymeric material that is combined with at least one active agent to form a highly viscous material, such as, for example with a viscosity of between 500,000 cP and 4,000,000 cP. Preferably the viscosity of the active agent containing material can be decreased by heating the active agent containing material while it is contained in, or passing through a dispensing pump according to the present invention.

In some embodiments, the punctal plug body is preferably impermeable to the active agent, meaning only an insubstantial amount of active agent can pass there through, and the punctal plug body has at least one opening through which the active agent is released. The opening may have a membrane or permeable material covering through which the active agent may pass in therapeutic amounts.

CONCLUSION

The present invention, as described above and as further defined by the claims below, provides methods of processing punctal plugs and apparatus for implementing such methods, as well as punctal plugs formed thereby.

What is claimed is:

1. A pulsatile delivery device of an active agent, the device comprising:
    a tube inserted into a cavity of a punctal plug; and
    two or more discrete pulsatile delivery units arranged in a generally linear fashion within the tube, wherein the two or more discrete pulsatile delivery units comprise a core comprising the active agent and an encapsulation layer surrounding the core, the discrete pulsatile delivery units are spaced apart from one another and in a generally linear arrangement are arranged to release from the tube multiple pulses of active agent, wherein each respective pulse of active agent comprises a generally equal volume of active agent and each respective pulse of active agent comprises a generally equal concentration of active agent.

2. The pulsatile delivery device of claim 1 wherein the one or more pulsatile delivery units comprise water soluble encapsulated beads.

3. The pulsatile delivery device of claim 2 wherein the generally linear arrangement of the pulsatile delivery units limits exposure of pulsatile delivery units to tear fluid to one pulsatile delivery unit at a time.

4. The pulsatile delivery device of claim 2 further comprising a boundary layer between a first pulsatile delivery unit and a second pulsatile delivery unit.

5. The pulsatile delivery device of claim 2, wherein the active agent-containing material comprises poly(epsilon-caprolactone) and ethylene vinyl acetate.

6. The pulsatile delivery device of claim 5, wherein the poly(epsilon-caprolactone) and ethylene vinyl acetate are each present in an amount of about 50 weight percent.

7. The pulsatile delivery device of claim 2, wherein the tube comprises a first pulsatile delivery unit comprising a first active-agent containing material comprising a relatively low concentration of the active agent and a second pulsatile delivery unit comprising a second active-agent containing material comprising a relatively high concentration.

8. The pulsatile delivery device of claim 2, additionally comprising an initial pulsatile delivery until delivering an amount of active agent greater than amounts of active agent delivered by subsequent delivery units.

9. The pulsatile delivery device of claim 1 further comprising a boundary layer between a pulsatile delivery unit and an opening in the cavity of the punctal plug.

10. The pulsatile delivery device of claim 9 wherein the boundary layer comprises a biodegradable membrane.

11. The pulsatile delivery device of claim 9 wherein the boundary layer comprises a semi-porous membrane.

12. The pulsatile delivery device of claim 9 wherein the boundary layer comprises a mesh.

13. The pulsatile delivery device of claim 1 wherein the core comprises an active agent-containing material and a phase separated inclusion.

14. The pulsatile delivery device of claim 1 wherein the core comprises an active agent-containing material and a destabilizing inclusion.

15. The pulsatile delivery device of claim 1 wherein the core comprises an active agent-containing material and a stabilizing inclusion.

16. The pulsatile delivery device of claim 1 wherein the punctal plug additionally comprises a punctal plug body and a cavity within the punctal plug body.

17. The pulsatile delivery device of claim 16 wherein the punctal plug additionally comprises an access opening to the cavity from a position external to the body when the plug is inserted into a punctum.

18. The pulsatile delivery device of claim 16 wherein the punctal plug additionally comprises a seal across the opening to the cavity, blocking access to the cavity from a position external to the body when the plug is stored outside a punctum.

* * * * *